(12) United States Patent
Foster et al.

(10) Patent No.: US 11,054,364 B2
(45) Date of Patent: Jul. 6, 2021

(54) APPARATUS AND METHODS FOR HANDLING AND SPECTROPHOTOMETRY OF SMALL LIQUID SAMPLES

(71) Applicant: Thermo Finnigan LLC, San Jose, CA (US)

(72) Inventors: Greg A. Foster, Redwood City, CA (US); Daniel Lopez Ferrer, San Carlos, CA (US)

(73) Assignee: THERMO FINNIGAN LLC, San Jose, CA (US)

( * ) Notice: Subject to any disclaimer, the term of this patent is extended or adjusted under 35 U.S.C. 154(b) by 213 days.

(21) Appl. No.: 16/222,851

(22) Filed: Dec. 17, 2018

(65) Prior Publication Data

US 2020/0191705 A1 Jun. 18, 2020

(51) Int. Cl.
*G01N 21/25* (2006.01)
*G01N 21/31* (2006.01)
(Continued)

(52) U.S. Cl.
CPC .......... *G01N 21/255* (2013.01); *G01N 21/31* (2013.01); *G01N 33/6848* (2013.01);
(Continued)

(58) Field of Classification Search
CPC .. G01N 21/255; G01N 21/31; G01N 33/6848; G01N 35/0099; G01N 35/1095;
(Continued)

(56) References Cited

U.S. PATENT DOCUMENTS

| 4,422,151 A | 12/1983 | Gilson |
| 4,643,580 A | 2/1987 | Gross et al. |

(Continued)

FOREIGN PATENT DOCUMENTS

| CN | 100371710 C | 8/2006 |
| EP | 3546922 A1 | 10/2019 |

(Continued)

OTHER PUBLICATIONS

Ritchie, R.F. Whicher, J.T. Serum Proteins. Published Sep. 15, 2006 In Encyclopedia of Analytical Chemistry editors R.A. Meyers and M.A. Evenson, p. 17 (Year: 2006).*

(Continued)

*Primary Examiner* — Jennifer Wecker
*Assistant Examiner* — Jonathan Bortoli
(74) *Attorney, Agent, or Firm* — Thomas F. Cooney (57) ABSTRACT

A system comprises: (a) a robotic arm; (b) a needle capillary coupled to the robotic arm; (c) a cell coupled to the robotic arm comprising: a housing; first and second windows disposed within the housing and defining a width of an internal chamber therebetween; a collimating lens optically coupled to the first window; a focusing lens optically coupled to the second window; an inlet port fluidically coupled to a first end of the internal chamber; and an outlet port fluidically coupled to a second end of the internal chamber; (d) a pump; (e) first and second tubings fluidically coupled, respectively, between the needle capillary and the inlet port and between the pump and the outlet port; (f) a light source; (g) a photodetector; and (h) first and second optical fibers optically coupled, respectively, between the light source and the collimating lens and between the photodetector and the focusing lens.

9 Claims, 9 Drawing Sheets

(51) Int. Cl.
*G01N 33/68* (2006.01)
*G01N 35/00* (2006.01)
*G01N 35/10* (2006.01)

(52) U.S. Cl.
CPC ..... *G01N 35/0099* (2013.01); *G01N 35/1095* (2013.01); *G01N 2201/068* (2013.01)

(58) Field of Classification Search
CPC .......... G01N 2201/068; G01N 35/109; G01N 35/1009; G01N 2035/1062; G01N 21/33; G01N 2021/0346; G01N 30/74
See application file for complete search history.

(56) References Cited

U.S. PATENT DOCUMENTS

| | | | |
|---|---|---|---|
| 4,910,402 A | | 3/1990 | McMillan |
| 5,434,664 A | | 7/1995 | Sapp |
| 5,734,468 A | * | 3/1998 | McNeal ................ B01L 3/021 356/244 |
| 5,988,236 A | | 11/1999 | Fawcett |
| 6,013,528 A | | 1/2000 | Jacobs et al. |
| 6,024,925 A | | 2/2000 | Little et al. |
| 6,240,984 B1 | | 6/2001 | Fawcett et al. |
| 6,342,948 B1 | | 1/2002 | Gilby |
| 8,664,617 B2 | | 3/2014 | Fortt et al. |
| 9,658,153 B2 | | 5/2017 | Goto et al. |
| 10,060,541 B1 | * | 8/2018 | Saetveit ................ F16K 11/10 |
| 2002/0095974 A1 | | 7/2002 | Gilson et al. |
| 2004/0241872 A1 | * | 12/2004 | Wegrzyn ............ B01J 19/0046 436/171 |
| 2006/0118723 A1 | * | 6/2006 | Kimata ................ G01N 21/05 250/339.12 |
| 2008/0101996 A1 | | 5/2008 | Daf |
| 2010/0150781 A1 | | 6/2010 | Ervin et al. |
| 2011/0182782 A1 | | 7/2011 | Dzuong |
| 2013/0280145 A1 | | 10/2013 | West et al. |
| 2014/0030751 A1 | | 1/2014 | Sharp |
| 2014/0373606 A1 | | 12/2014 | Kraiczek et al. |
| 2016/0266040 A2 | | 9/2016 | Bjornson et al. |
| 2018/0156726 A1 | * | 6/2018 | Liu ........................ G01J 3/4338 |

FOREIGN PATENT DOCUMENTS

| | | | | |
|---|---|---|---|---|
| WO | 2018/218163 A1 | | 11/2018 | |
| WO | WO2018218163 | * | 11/2018 | .............. B01J 19/00 |
| WO | WO-2018218163 A1 | * | 11/2018 | ........... G01N 21/631 |

OTHER PUBLICATIONS

Lang et al., "Development of NIST Standard Reference Material 2082, a Pathlength Standard for Measurements in the Ultraviolet Spectrum", Journal of Research of the National Institute of Standards and Technology, vol. 122, Article No. 33 (2017).

Avantes, "Mini Transmission Dip Probes", https://www.avantes.com/products/fiber-optics/item/252-mini-transmission-dip-probe, retrieved Apr. 3, 2019, 2 pages.

BioTek, "Quantitation of Peptides and Amino Acids with a Synergy™ HT using UV Fluorescence", Application Note, https://www.biotek.com/resources/docs/Synergy_HT_Quantitation_of_Peptides_and_Amino_Acids.pdf, 2003, pp. 1-8.

Fleischer et al., "Application of a Dual-Arm Robot in Complex Sample Preparation and Measurement Processes", Journal of Laboratory Automation 2016, vol. 21 (5), pp. 671-681.

Wang et al., "A remote flow cell for UV absorbance detection with capillary HPLC based on a single strand fiber optic", Analyst, 2000, 125, pp. 1061-1064.

* cited by examiner

APPARATUS AND METHODS FOR HANDLING AND SPECTROPHOTOMETRY OF SMALL LIQUID SAMPLES

TECHNICAL FIELD

The present disclosure relates to liquid handling and liquid handler apparatuses. In particular, the present disclosure relates to methods of combined liquid handling and spectrophotometry and to apparatuses which perform combined liquid handling and spectrophotometry.

BACKGROUND

Optical spectrophotometric techniques, including UV-visible (ultraviolet-visible) optical absorption spectroscopy and colorimetry, are used extensively in organic chemical and biochemical assays. Spectrophotometric methods provide some of the simplest and fastest ways to analyze the content of samples. Typically, an optical spectrophotometric measurement is preceded by one or more sample collection and preparation steps, the latter including steps such as possible cell lysis, filtration, precipitation, centrifugation, dilution, dispensing of reagents, mixing, heating, drawing of sample fractions, etc. Additional sample handling steps may be carried out subsequent to the optical spectroscopic measurement.

Typically, drug discovery, clinical and other biochemical research assay programs are carried out in parallel on a multitude (many thousands or tens of thousands) of samples and sample portions provided in liquid form. Therefore, for efficiency purposes, many of the sample preparation and handling steps are carried out by automated liquid handler apparatuses that draw samples from and dispense reagents to specialized containers that are arrayed in a regular geometric pattern. Such specialized containers include vials that are arrayed in a vial holder or in depression-like wells of a plate having a plurality of such wells. The specialized containers are generally small (e.g., microliter to milliliter capacity) in order to prevent the overall apparatus size from becoming unwieldy and for general ease of handling. The robotic liquid handler system may include one or more pipettes that are designed to mate with and/or dip into the sample containers for purposes of aspiration and dispensing and at least one mechanical carriage system for manipulating either the array of containers or the one or more pipettes in space.

Spectrophotometric measurements are generally carried out using different apparatus and, frequently, different sample containers that are incompatible with general robotic liquid handlers. Such analyses are usually carried out using quartz cuvettes having flat side walls or, recently as a result of high demand in the biopharmaceutical industry, using plate readers that are able to conduct measurements of samples held in multi-well plates. Unfortunately, when the analyses require sample preparation steps before the actual measurement, the integration of these steps with spectrophotometric analysis is quite challenging and expensive because of the difficulty of integrating plate readers into automated liquid handlers. Further, many times a sample cannot be reused for other purposes once the spectrophotometric measurement is complete.

The above-noted challenges are further exacerbated for samples that are very difficult to obtain and/or are available only in very small quantities (e.g., less than or equal to 200 microliters), such as medical biopsies and single blood droplets drawn from small laboratory animals. A spectrophotometer usually requires a minimum volume for accurate readings that an analyte might not be able to accommodate due to the limited amount of sample available. In such cases, a user must often make a tradeoff between the accuracy of the reading and how much sample can be made available for the spectrophotometric assay.

SUMMARY

To overcome the above-described challenges, a combined liquid handling and photometric system has been developed. The novel system includes a flow cell spectrophotometer that fits in a liquid dispenser system within an automated liquid handler. This system enables high throughput, automated UV readings using minimal volumes (down to 3-5 µL), no sample consumption and an accuracy equal or better than current commercial systems. The novel system is an easy to use platform that provides a consistent protein and polypeptide concentration and that enables the development of standardized methods for preparing samples for mass spectrometric analysis.

According to a first aspect of the present teachings, a combined liquid handling and photometric system is provided, the system comprising: (a) a robotic arm; (b) a needle capillary coupled to the robotic arm; (c) a cell coupled to the robotic arm comprising: a housing; first and second windows disposed within the housing and defining a width of an internal chamber therebetween; a collimating lens optically coupled to the first window; a focusing lens optically coupled to the second window; an inlet port fluidically coupled to a first end of the internal chamber; and an outlet port fluidically coupled to a second end of the internal chamber; (d) a pump; (e) first and second tubings fluidically coupled, respectively, between the needle capillary and the inlet port and between the pump and the outlet port; (f) a light source; (g) a photodetector; and (h) first and second optical fibers optically coupled, respectively, between the light source and the collimating lens and between the photodetector and the focusing lens. According to some embodiments, one or both of the group consisting of the light source and the photodetector may be fastened to the robotic arm. According to various embodiments, the internal chamber may comprise a volume of less than or equal to 200 micro-liters (µL) or even less than or equal to 100 µL. In various embodiments, the fluidic outlet port is disposed substantially vertically above the fluidic inlet port and the needle capillary is disposed below the fluidic inlet port. According to some embodiments, the width of the internal chamber is in the range 1.0 to 1.5 millimeters (mm). According to some embodiments, the light source, first optical fiber, collimating lens and first window are configured such that, in operation, a collimated light beam is provided between the first and second windows that has a total volume in the range of 3-5 mm$^3$ between the two windows. In various embodiments, the system may further comprise: a multiport valve fluidically coupled to both the fluidic pump and the second tubing; a second fluidic pump fluidically coupled to the multiport valve; and a source of a washing solution fluidically coupled to the second pump. In various embodiments, a set of fasteners, gaskets and o-rings may be provided so as to ensure that the windows are sealed against the housing in a leak-tight fashion up to internal chamber pressures of 10 bars.

In accordance with a second aspect of the present teachings, an analytical method comprises: aspirating a sample upward through a needle capillary into a chamber having side portions that are defined by a first and a second window; causing a light beam to pass through the sample between the first and second windows; detecting a quantity of light of the light beam that passes through the sample and the first and second windows; determining an optical absorbance of the sample from the detected quantity of light; determining a concentration of an analyte in the sample from the determined optical absorbance; determining a quantity of the sample to dispense into an analytical apparatus based on the determined analyte concentration; and dispensing the determined quantity of the sample from the chamber into the analytical apparatus through the needle capillary. According to various embodiments, the analytical apparatus may be one of the group consisting of: a solid phase extraction (SPE) cartridge, a chromatograph and a mass spectrometer. According to some embodiments, the step of detecting the quantity of light of the light beam that passes through the sample and the first and second windows comprises detecting a quantity of light of approximate wavelength 280 nanometers, which corresponds to optical absorbance of the sample that is attributable to tryptophan. In such instances, the subsequent step of determining the quantity of the sample to dispense into the analytical apparatus comprises estimating a quantity of the sample that contains a predetermined number of moles of polypeptides and proteins within the sample, wherein the estimated quantity of the sample is based on the optical absorbance of the sample that is attributable to tryptophan.

BRIEF DESCRIPTION OF THE DRAWINGS

The above noted and various other aspects of the present invention will become apparent from the following description which is given by way of example only and with reference to the accompanying drawings, not necessarily drawn to scale, in which.

DETAILED DESCRIPTION

The following description is presented to enable any person skilled in the art to make and use the invention, and is provided in the context of a particular application and its requirements. Various modifications to the described embodiments will be readily apparent to those skilled in the art and the generic principles herein may be applied to other embodiments. Thus, the present invention is not intended to be limited to the embodiments and examples shown but is to be accorded the widest possible scope in accordance with the features and principles shown and described. To fully appreciate the features of the present invention in greater detail, please refer to FIGS. 1A, 1B, 2-4, 5A, 5B and 6.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that, for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise.

Unless otherwise defined, all technical and scientific terms used herein have the meaning commonly understood by one of ordinary skill in the art to which this invention belongs. In case of conflict, the present specification, including definitions, will control. It will be appreciated that there is an implied "about" prior to the quantitative terms mentioned in the present description, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. As used herein, "a" or "an" also may refer to "at least one" or "one or more." Also, the use of "or" is inclusive, such that the phrase "A or B" is true when "A" is true, "B" is true, or both "A" and "B" are true. As used herein, the term "substantially", when used as an adjective or adverb to modify a stated quantity, a stated orientation of a component (such as vertical or horizontal), or a stated disposition of a component (such as vertically above) should be understood to mean that the actual quantity, orientation or disposition is within five percent, either plus or minus, of the stated value of the quantity, orientation or disposition. As used herein, the terms "approximate" and "approximately", when used as an adjective to modify a stated quantity should be understood to mean that the actual quantity is within five percent, either plus or minus, of the stated value of the quantity.

Figure 1A:
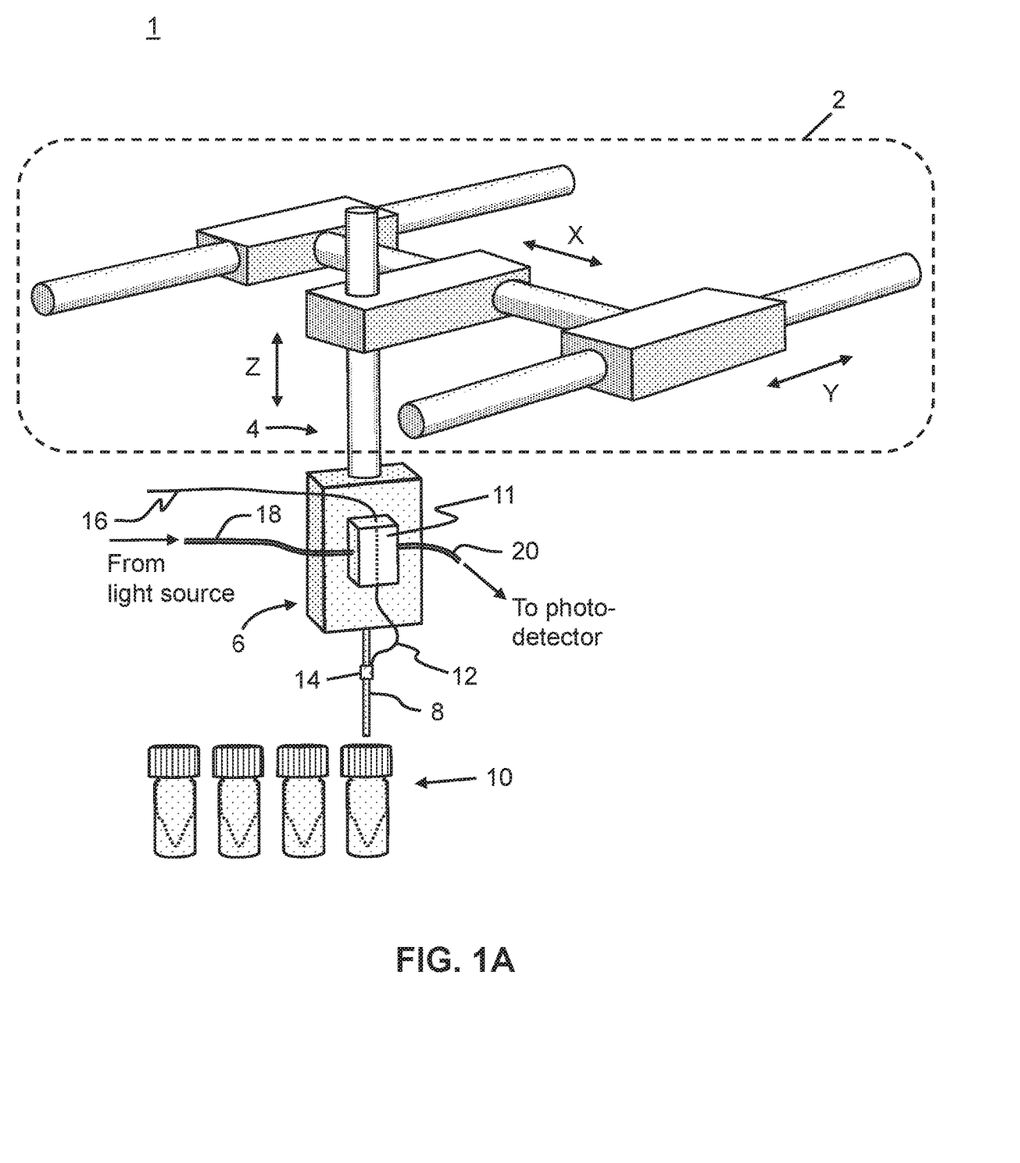
FIG. 1A is a schematic diagram of a portion of an apparatus, in accordance with the present teachings, for combined liquid handling and spectrophotometric analysis of liquid samples of volume 3 micro-liters to 100 micro-liters.

FIG. 1A is a schematic diagram of a portion of an apparatus 1, in accordance with the present teachings, for combined liquid handling and spectrophotometric analysis of liquid samples of volume greater than or equal to 3 micro-liters (µL) and, preferably, in the range from 3 µL to 100 µL. The apparatus includes a conventional mechanism for manipulating a needle capillary 8 that is attached to a robotic arm 4 that part of a conventional robotic assembly 2 that is able to re-position the needle capillary 8, within limits, along any or all of three Cartesian co-ordinate axes X, Y or Z, where, by convention, the Z-axis is taken as vertical.

According to the present teachings, the robotic arm 4 is mechanically coupled to an optical/flow cell 11 by means of a mounting structure or adaptor 6 such as a block, plate, bracket, etc. The needle capillary 8 is also rigidly attached to the mounting structure or adaptor 6 in a fashion such that the needle capillary extends downward relative to the lowermost portion of the optical/flow cell 11. One or more sample containers 10 are positioned such that the robotic assembly 2 is able to position the arm 4 and its attached mounting structure or adaptor 6 so as to insert the needle capillary into any one of the sample containers 10. Preferably, each of the sample containers 10 comprises an internal downward-narrowing conical well for precise internal positioning of a small amount of liquid, such as a single droplet of a sample. Similarly, one or more reagent containers (not shown) may likewise be positioned such that the robotic assembly 2 is able to position the arm 4 and mounting structure or adaptor 6 so as to insert the needle capillary into any one of the reagent containers. The reagent containers, if present, may comprise a different size or shape than the sample containers. The needle capillary comprises an outer diameter that permits it to penetrate to within 0.5 mm of the bottom of the conical well and, preferably, that mates, in a leak-tight fashion, with an inlet port receptacle of a standard chemical separation or analytical apparatus, such as a conventional solid phase extraction (SPE) cartridge, an injector port of a chromatograph or an inlet port of a mass spectrometer.

Figure 1B:
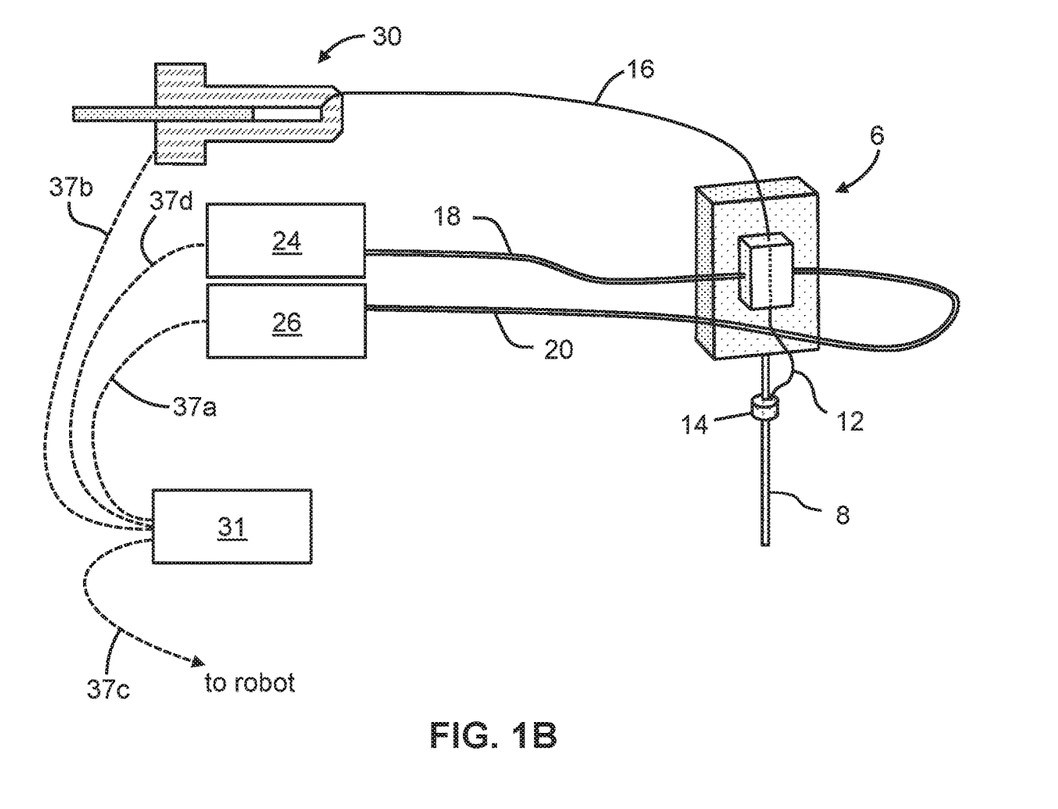
FIG. 1B is a schematic diagram of another portion of the apparatus of FIG. 1A.

FIG. 1B is a schematic diagram of another portion of the apparatus of FIG. 1A. A top end of the needle capillary 8 is fluidically coupled to a lower end of a tubing 12 via a fluidic coupling 14. A top end of the tubing 12 is fluidically coupled, at a bottom portion of the optical/flow cell 11, to internal fluidic channels (not shown in FIG. 1A) of the optical/flow cell 11. The internal channels of the optical/flow cell 11 are fluidically coupled, at a top portion of the optical/flow cell 11, to a first end of a second tubing 16. The opposite end of the tubing 16 is fluidically coupled to a fluid pump 30, which is preferably a syringe pump. In operation, withdrawal of a piston of the syringe pump from its enclosing chamber creates a pressure deficit in the tubing 16, internal channels, tubing 12 and needle 8, which is able, when the bottom end of the needle is immersed in a sample, to withdraw at least a portion of the sample from its container and into the needle and internal channels of the optical/flow cell 11. Subsequent, opposite motion of the syringe pump piston then urges the sample portion in the opposite direction through the optical/flow cell 11, tubing 12 and needle capillary 8 so as to thereby dispense the sample portion into the same or a different container.

The device 11 is herein referred to as an "optical/flow cell" because it provides the capability for conducting spectrophotometric measurements while retaining the capability as a simple conduit for temporary storage of samples, reagents or mixtures thereof between aspiration and dispensing steps. Thus, the device 11 is not only a measurement apparatus but also a component of the general dispensing portion of a sample preparation system or general liquid handling system. For this purpose, the inventors have utilized a modified form of a device that is commercially available from CTC Analytics AG of Zwingen, Switzerland.

The apparatus 1 includes a controller 31 (FIGS. 1B, 1C) that is electronically coupled to the photodetector 26, the pump 30 and the robot 2 by means of electronic 37a, 37b and 37c, respectively. The controller 31 receives data from the photodetector and also co-ordinates the operation of those various devices by sending commands to the devices. The controller 31 may also be electronically coupled to the light source 24 by means of electronic line 37d. The controller 31 includes at least one central processing unit ("CPU") coupled to electronic memory. Each CPU is typically implemented in hardware using circuit logic disposed on one or more physical integrated circuit devices or chips. Each CPU may be or may include one or more microprocessors, microcontrollers, field programmable gate arrays, or ASICs, while the electronic memory may include random access memory ("RAM"), dynamic random access memory ("DRAM"), static random access memory ("SRAM"), flash memory, and/or another digital storage medium, and also typically implemented using circuit logic disposed on one or more physical integrated circuit devices, or chips. As such, the memory may be considered to include memory storage physically located elsewhere, e.g., any cache memory in the at least one CPU, as well as any storage capacity used as a virtual memory, e.g., as stored on a mass storage device or as stored on a local network or on the Internet, as coupled to the controller through at least one network interface. The memory may be provided with computer-readable electronic instructions (e.g., a program) that, when accessed by and executed by the controller's logic circuitry, cause the controller to 31 operate the hardware components of the apparatus 1 so as to execute the below-described spectrophotometric and liquid handling methods in accordance with the present teachings.

Figure 1C:
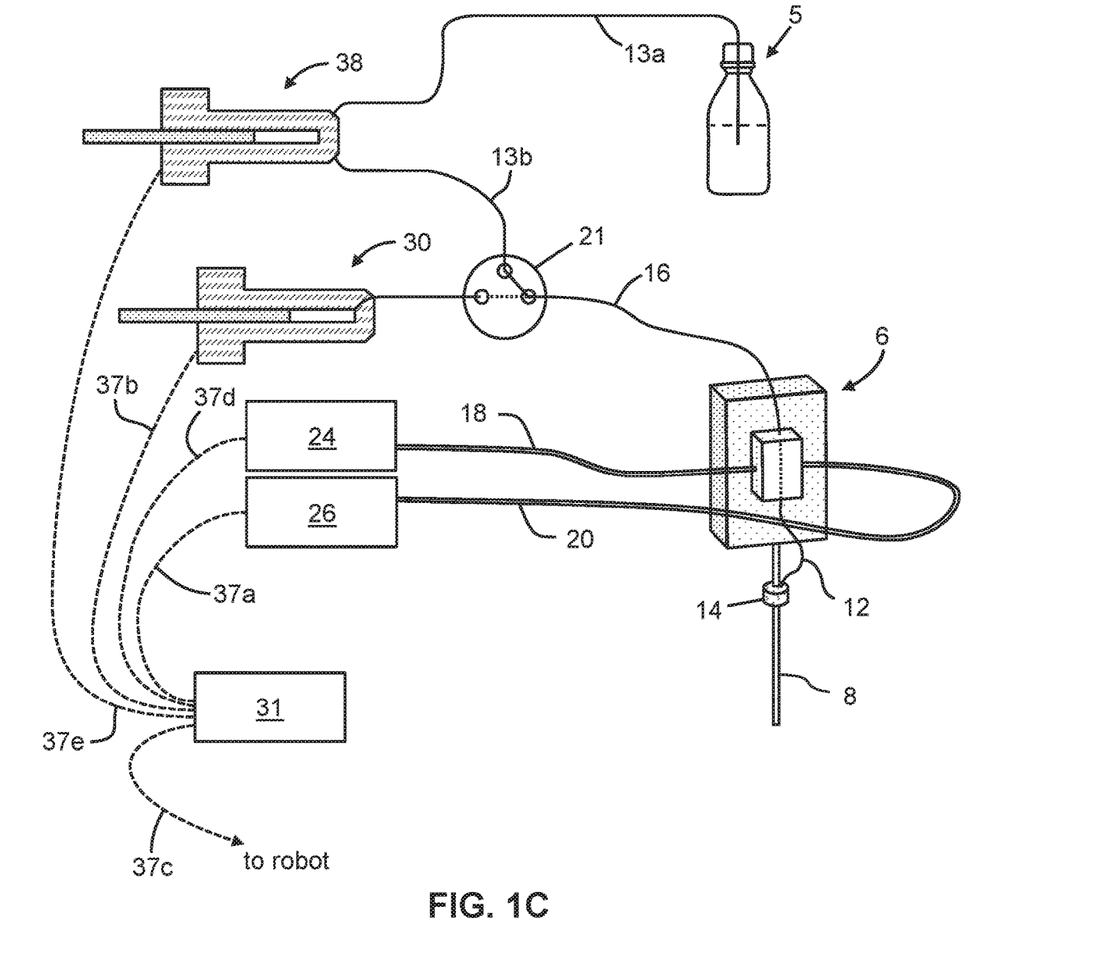
FIG. 1C is a schematic diagram of an alternative variation of the other portion of the apparatus of FIG. 1B.

FIG. 1C is a schematic diagram of an alternative variation to the apparatus portion of FIG. 1B. In this variation, a second pump 38, which may be a syringe pump or any other suitable pump such as a reciprocating pump, a peristaltic pump, etc., it used to draw a wash solution from a wash solution supply 5 and to pump the wash solution through additional tubings 13a and 13b and one or more multiport valves 21. The second pump 38 is electronically coupled to the controller 31 by means of electronic line 31e. According to this hardware configuration, washing of the system is performed by operating the pump 38 and the valve(s) 21 so as to cause the wash solution to flow, for example, as indicated by the solid line pathway through the depicted valve such that the wash solution flows through tubing 13a, pump 38 and tubing 13b to valve 21 and through valve 21 to tubing 16. Otherwise, when the pump 30 is actively aspirating or dispensing samples, the valve(s) 21 are configured so as to route fluids, for example, according to the dotted line pathway through the depicted valve, such that the pump 30 is fluidically coupled to tubing 16.

The optical/flow cell 11 is also optically coupled to a first optical fiber 18 and a second optical fiber 20, the two optical fibers being optically coupled to different sides of an internal chamber or channel of the optical/flow cell 11 as described in greater detail below. The first optical fiber 18 is configured to receive light that is emitted from a light source 24, such as a laser, a diode or a lamp, and to transmit the light to a first side of the internal chamber or channel. In operation of the apparatus 1, the light received from the first optical fiber 18 passes through a sample portion within the chamber or channel and the portion of the light that passes through the sample portion is focused into the second optical fiber 20 at a second side of the chamber or channel that is opposite to the first side. The second optical fiber 20 transmits this light to a photodetector 26 for spectral analysis.

The light source 24 and the photodetector 26 may be either as simple or as complex as required for making the measurements of interest. Preferably the light source if of a type that emits multiple wavelengths such as either an incandescent lamp or a metal-vapor or nobel-gas vapor lamp. However, the light source 24 may comprise a laser if measurements are to be made only within a restricted wavelength range. The detector 26 may a single photodiode. In such instances, one or more optical bandpass filters may be disposed within the optical system (e.g., at the light source, between the sample and a one or the optical fibers, at the detector, etc.) so that the detector and possibly the sample are only exposed to a restricted wavelength range or ranges. If multiple bandpass filters are employed, they may be configured to be interchangeable with one another so that different measurements correspond to different wavelengths. Alternatively, if optical spectra are to be measured, the detector may comprise a plurality of individual light detectors that are configured such that different detectors are simultaneously exposed to different light wavelengths. Such a detector will generally include wavelength dispersive components such gratings, prisms or wavelength-dependent beam splitters, together with additional beam-steering components.

Figure 2:
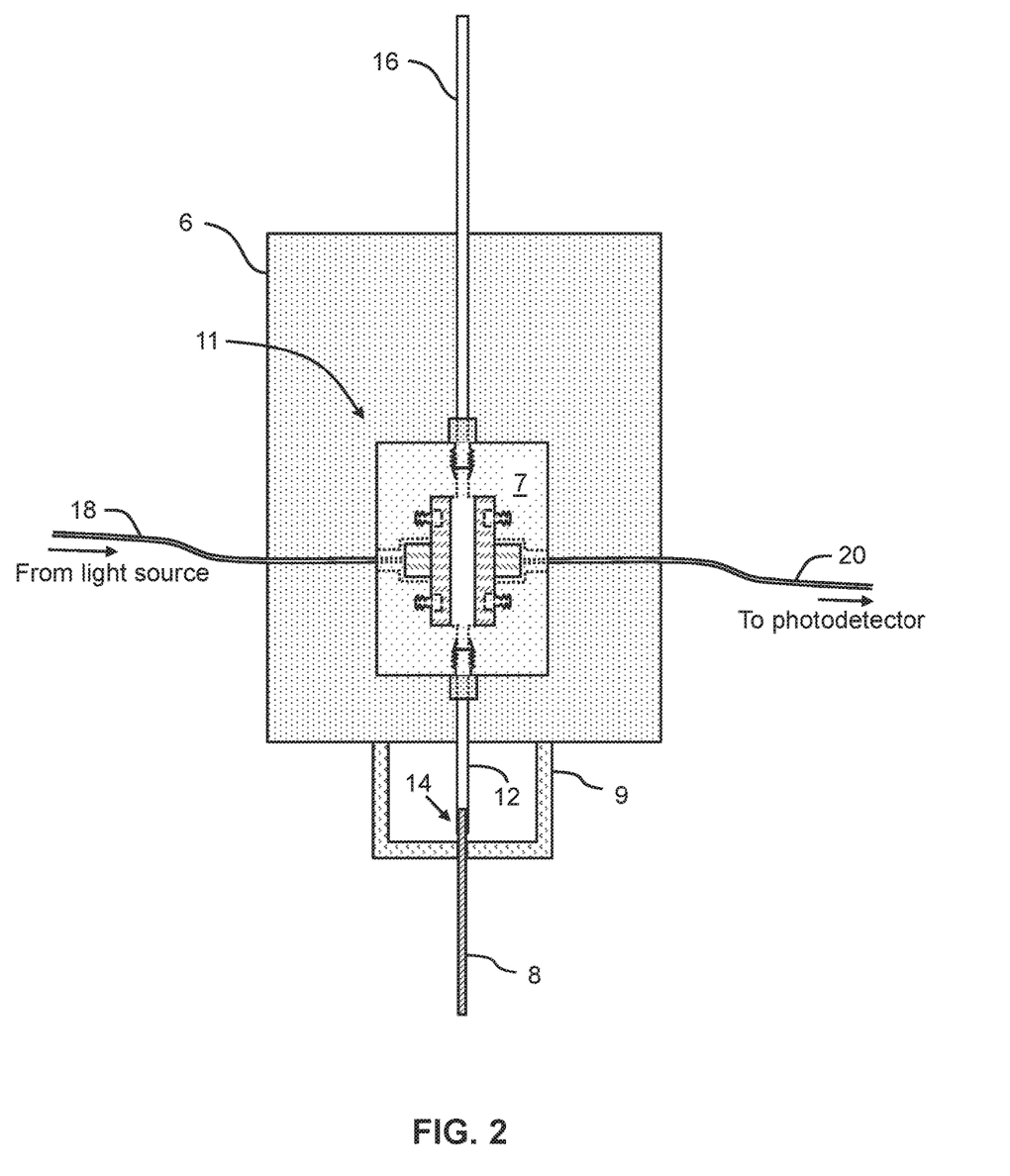
FIG. 2 is a schematic diagram of a spectrophotometric cell assembly as may be utilized in apparatuses in accordance with the present teachings.
Figure 3:
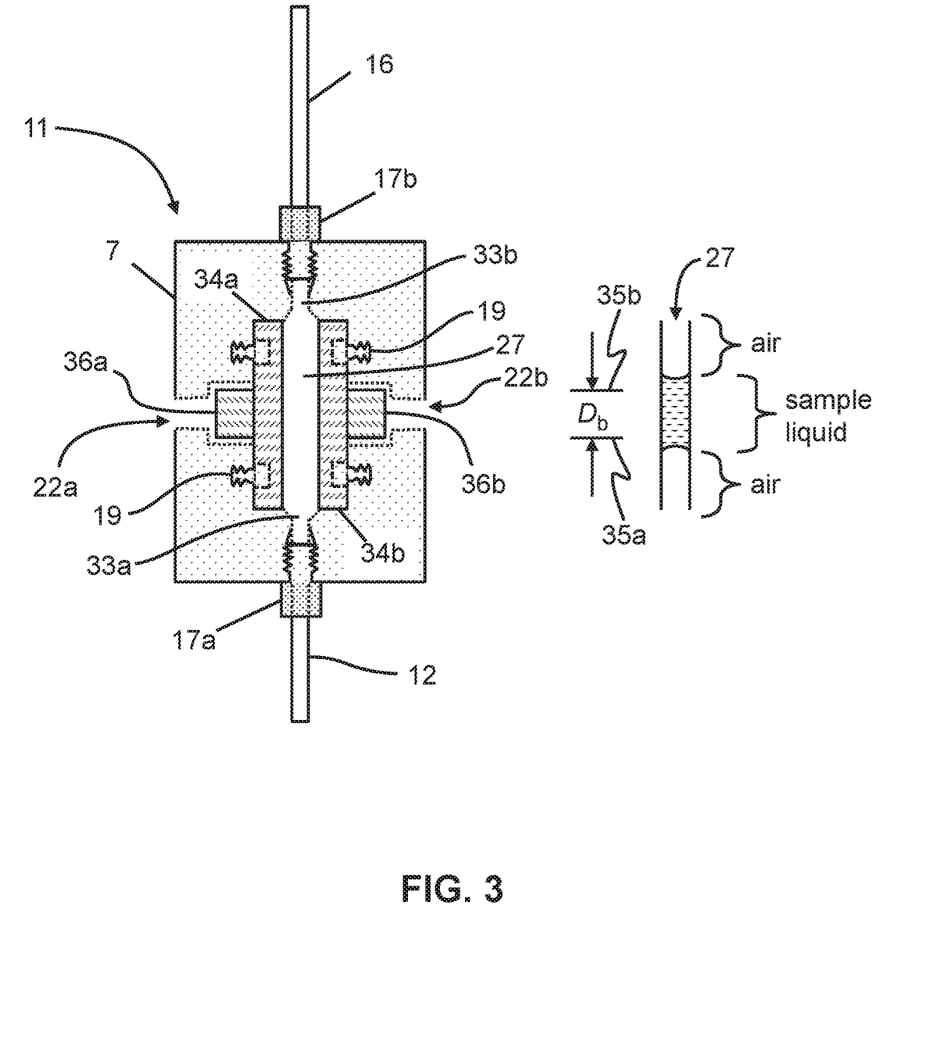
FIG. 3 is a schematic diagram of the spectrophotometric cell, fluidic connections and optical components of the assembly of FIG. 2.

FIG. 2 is an enlarged schematic cross-sectional diagram of the optical/flow cell 11 and the mounting structure or adaptor 6 to which it is attached. The optical/flow cell 11 comprises an optical/flow cell housing 7 that is mechanically coupled to the robotic arm 4 by the mounting structure or adaptor 6. FIG. 3 is a further enlarged schematic cross-sectional diagram of the optical/flow cell housing 7, absent the holder block and optical fibers, but together with the various associated fluid channels, fluidic couplings and optical components. In the illustrated example, the needle capillary 8 is rigidly attached to the mounting structure or adaptor 6 by means of a bracket 9 suspended from the bottom portion of the mounting structure or adaptor 6. However, the rigid attachment may be made by any other suitable mechanical coupling between the needle capillary 8 and the mounting structure or adaptor 6.

The tubing 12 is fluidically coupled to a lowermost channel 33a in the optical/flow cell housing 7 by means of a high pressure threaded fluidic fitting 17a (such as a fitting used in High Pressure Liquid Chromatography, abbreviated HPLC). Likewise the tubing 16 is fluidically coupled to an uppermost channel 33b in the optical/flow cell housing 7 by means of a similar threaded fitting 17b. The channels 33a and 33b are fluidically coupled to and expand into a chamber 27 within the optical/flow cell housing 11. The first optical fiber 18 passes through a first bore 22a that extends through the the optical/flow cell housing 7. The other optical fiber 20 likewise passes through a bore 22b. Each of the needle capillary 8, tubing 12 and channels 33a, 33b comprises an internal diameter of, preferably, less than or equal to 500 μm.

FIG. 3 shows the dispositions of optical lenses 36a, 36b within the first and second bores 22a, 22b, respectively. The first lens 36a is a collimating lens that is optically coupled to an end face first optical fiber 18 (not illustrated in FIG. 3) and that re-shapes light received from that fiber into a collimated beam that passes into the chamber 27 through a first window 34a. The sides of the chamber 27 are defined by a separation gap between the first window 34a and a second window 34b, both of which are disposed within the optical/flow cell housing 7. In operation, a portion of (or all of) a fluid sample that is disposed within the chamber 27 attenuates a portion of the collimated light. The attenuated collimated light then passes through second window 34b and is intercepted by second optical lens 36b. The second lens 36b is optically coupled to the second optical fiber 20 (not illustrated in FIG. 3) and focuses the intercepted light into an end face of that fiber. The optical fiber 20 transmits the intercepted attenuated light to photodetector 26 for spectral analysis. The result of the analysis is an optical transmittance or absorbance measurement. The various optical components (fibers, lenses, windows, etc.) should be chosen so as to be transparent to the wavelengths of light which are to be detected.

The faces of the windows 34a, 34b that bound the separation gap are nearly parallel to one another but, preferably, are not precisely parallel in order to avoid inadvertent etalon effects. Preferably, the width of the gap between the windows 34a, 34b is in the range of 1.0 mm to 1.5 mm and the diameter of the collimated beam, $D_b$ (see FIG. 3) is in the range of 1.50 mm to 2.50 mm, thereby yielding an illuminated volume, within the chamber 27, that is in the range of 3-5 $mm^3$. Thus, under such conditions, each optical measurement is obtained from a volume of sample in the approximate volume range of 3-5 μL. Note that the "illuminated volume" is defined as the region within the chamber 27 (i.e., between the windows 34a, 34b) through which the collimated beam passes, when the apparatus is in operation. The total volume of the chamber 27 may be less than 100 μL.

The windows 34a, 34b are secured to the optical/flow cell housing 7 by fasteners 19, such as screws. The physical boundaries between the windows 34a, 34b and the optical/flow cell housing 7, between the fasteners 19 and the windows 34a, 34b and between the fasteners 19 and the housing 7 are all sealed so as to prevent sample leakage. Preferably, the sealing is sufficient to prevent any sample leakage at internal chamber pressures up to and including 10 bars (1 mPa) of pressure, since such pressures are expected to develop as a result of back-pressure when the capillary needle is inserted into and is used to inject a sample into an inlet port of a chemical separation cartridge, such as a solid phase extraction (SPE) cartridge, that has significant internal flow resistance. The sealing up to 10 bars of pressure may be effected by means of a gasket (not shown) disposed between each window 34a, 34b and its respective seating surface and the optical/flow cell housing 7 and by means of by multiple o-rings (not shown) disposed about the shaft of each screw 19.

In operation of the apparatus 1, the pump 30 is operated such that at least a portion of a fluid sample is aspirated into the chamber 27 through needle capillary 8, tubing 12 and lowermost channel 33a of the optical/flow cell housing 7. It is generally only necessary to ingest the liquid sample portion into the chamber 27 to an extent such that the uppermost meniscus is entirely above the level 35b indicated in FIG. 3, which corresponds to the uppermost boundary of the illuminated volume within chamber 27. However, there should be a sufficient amount of ingested sample such that the lowermost meniscus is below the level 35a, which corresponds to the lowermost boundary of the illuminated volume. If the piston of the pump 30 is driven by a stepper motor, then the number of steps required to bring the upper meniscus to the appropriate level (after immersion of the lower tip of the needle capillary 8 within a sample) may be pre-determined prior to operation of the apparatus 1 with actual samples. Such a syringe pump may be operated so as to cause fluid flow rates as slow as 0.03 μL per second. Alternatively, the correct position of the sample portion in the chamber 27 may be determined during operation by continuous monitoring of light returning to photodetector 26 at the same time that a sample portion is being ingested into the chamber. Such monitoring may be performed either automatically or by a human operator.

Once an appropriate quantity of sample has been ingested, the action of the pump 30 is stopped such that the sample portion remains in position in the chamber 27 and an optical measurement is made. After measurement, all or a portion of the sample may be dispensed back into its original container or, alternatively, injected or infused into an inlet port of a chromatograph or mass spectrometer apparatus. The dispensing operation is performed by reversing the operation of the pump 30. Preferably, the apparatus 1 and the optical/flow cell housing 7 are disposed in an orientation such that the liquid sample portion is ingested into the chamber 27 in an upward direction and such that the sides of the chamber are substantially vertical. Such a configuration helps to prevent air bubbles from interfering in the optical transmittance measurements. In those instances in which the total available sample volume is in the range 3-5 μL, then the entire sample will be ingested into the chamber 27 as illustrated on the right hand side of FIG. 3.

Figure 4:
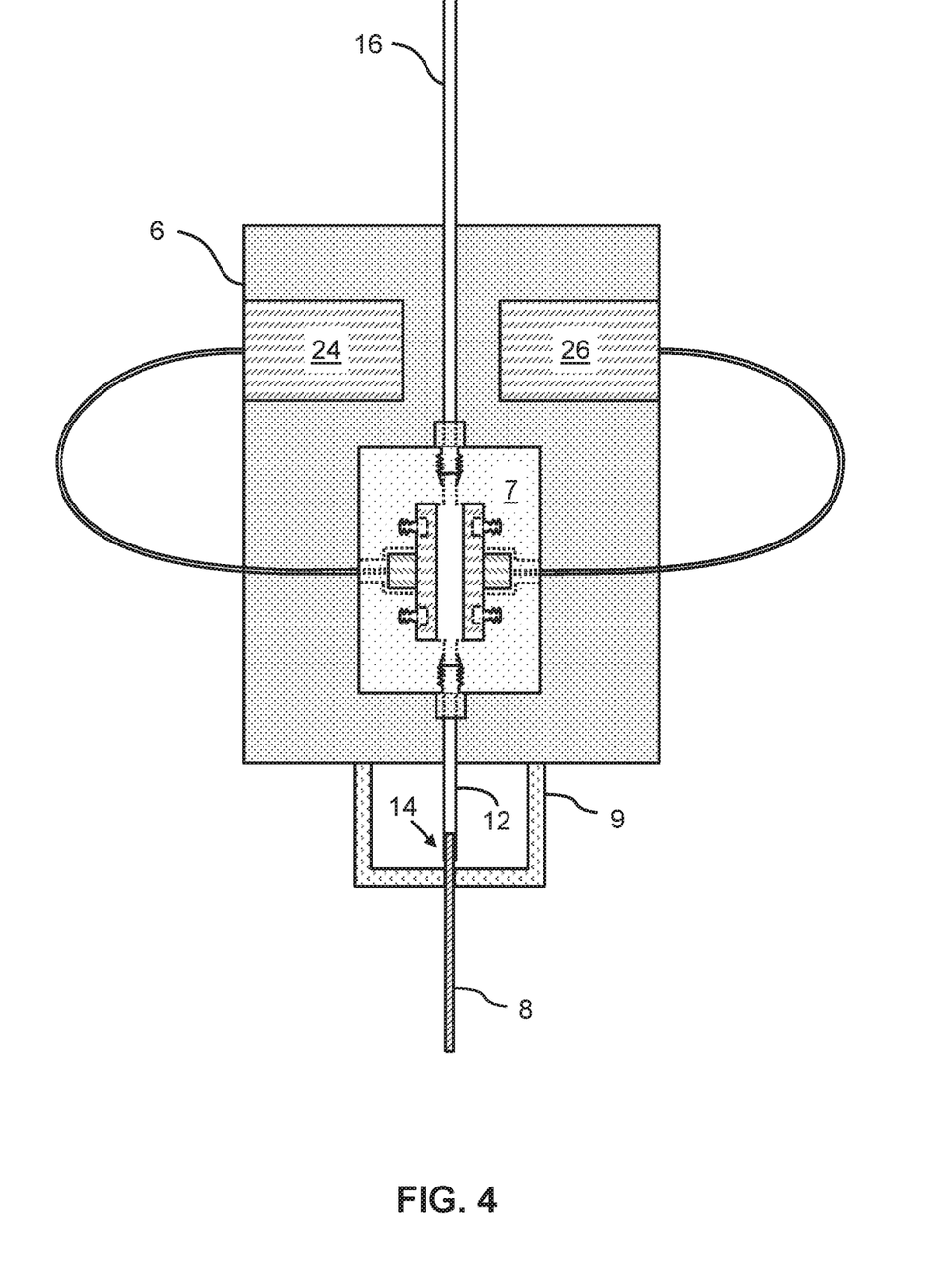
FIG. 4 is a schematic diagram of an alternative configuration of optical components, comprising a spectrophotometric cell and an attached light source and optical detector, as may be utilized in apparatuses in accordance with the present teachings.

FIG. 4 is a schematic diagram of an alternative configuration of optical components in accordance with the present teachings and as may be employed in accordance with methods of the present teachings. The apparatus configuration illustrated in FIG. 4 is generally similar to the configuration shown in FIG. 2 except that the light source 24 and photodetector 26 are attached to the mounting structure or adaptor 6 (or possibly directly to the robotic arm 4) such that the light source and photodetector move together with the arm and mounting structure or adaptor during normal operation in which the needle capillary 8 is continually moved from one sample container 10 to another such container. The configuration illustrated in FIG. 4 prevents entanglement and/or flexing of the optical fibers during normal operation.

Figure 5A:
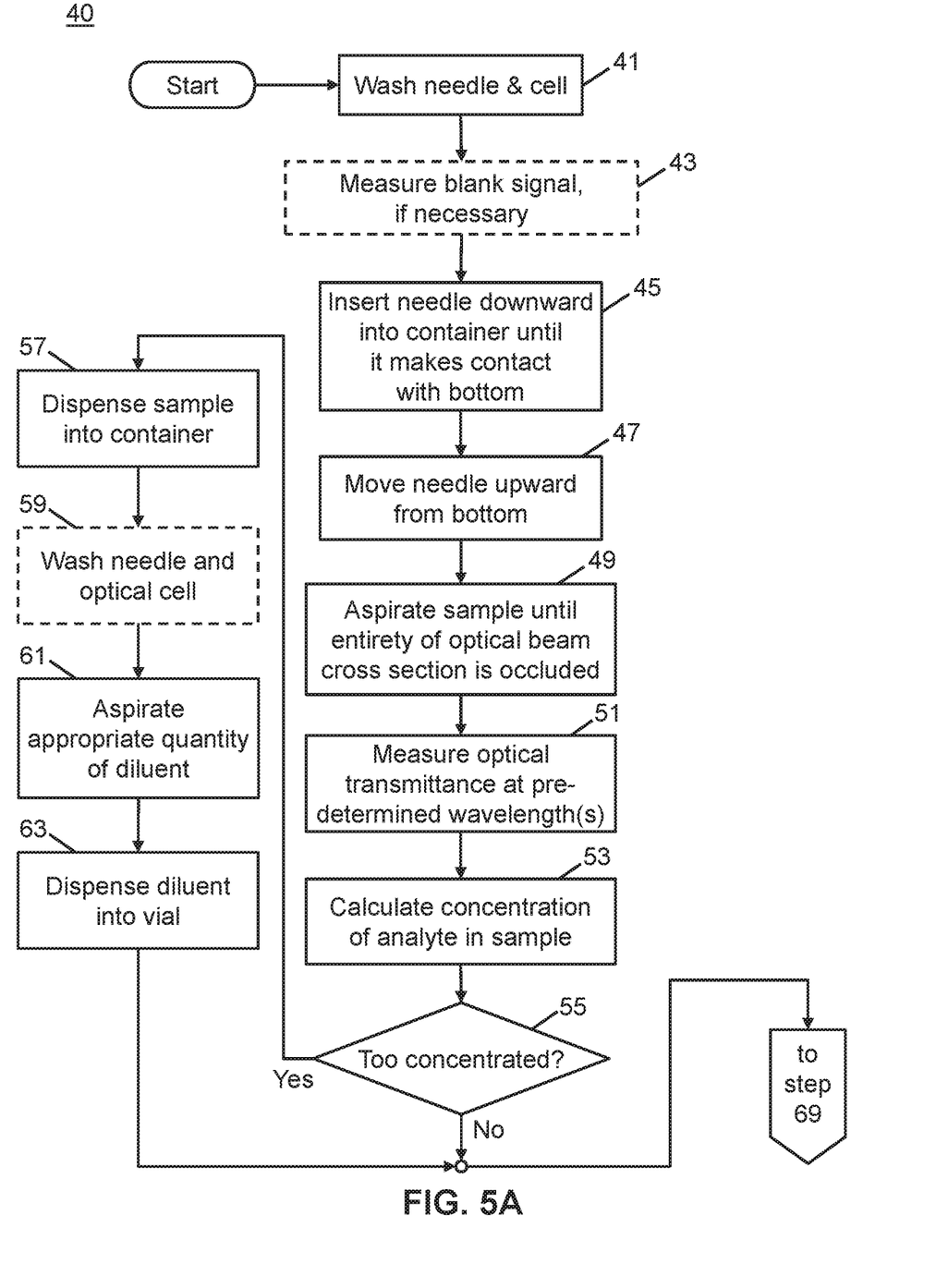
FIGS. 5A-5B are two partial views of a flow diagram of a method, in accordance with the present teachings, of using a combined liquid handling and spectrophotometric apparatus to determine a total concentration of a class of compounds within a sample and to dispense, based on the determined total concentration, a quantity of the sample to for further handling, processing or analysis.
Figure 5B:
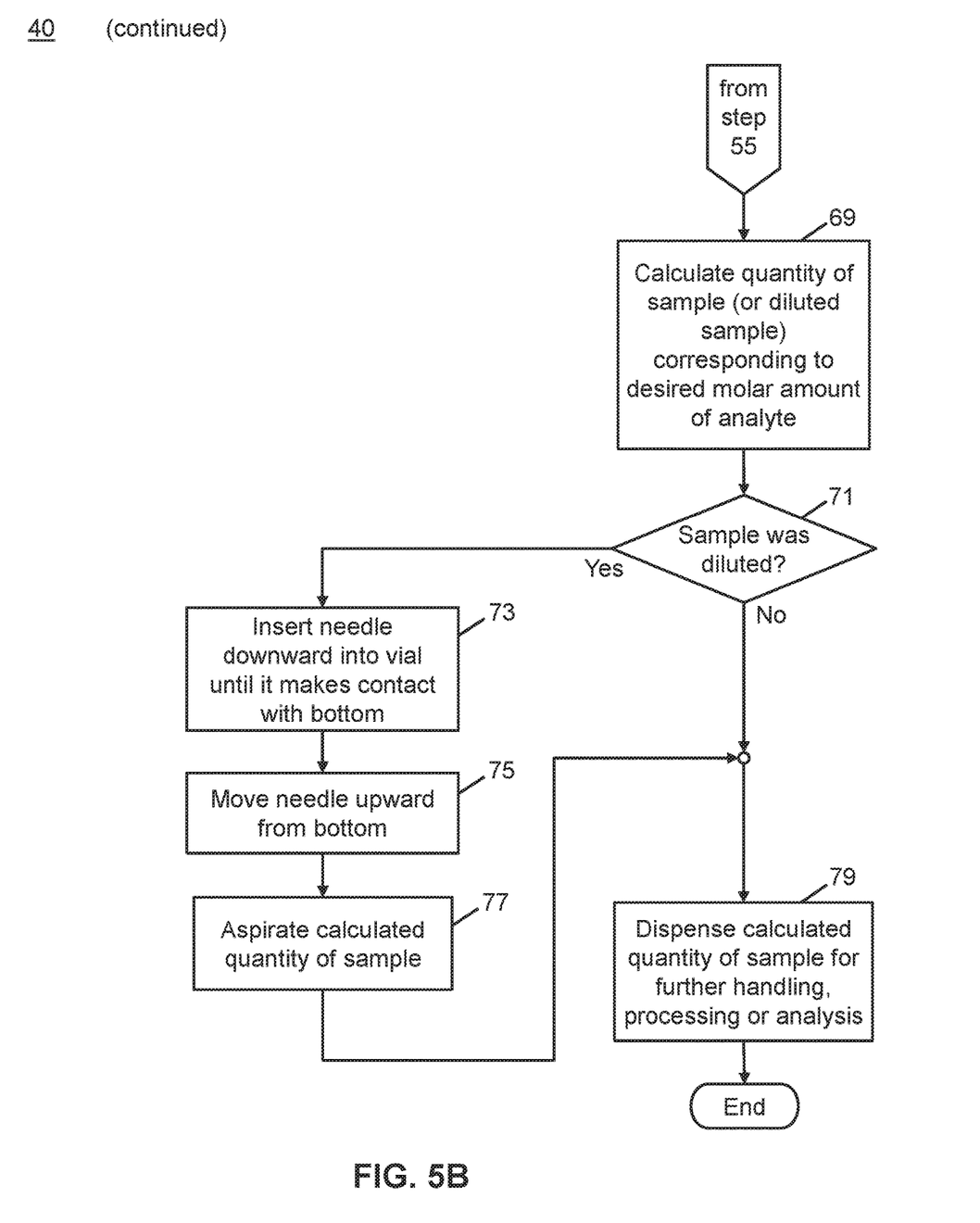

FIGS. 5A-5B are two partial views of a flow diagram of an operational method 40, in accordance with the present teachings. Steps 41 through 55 of the method are depicted on FIG. 5A and subsequent steps 69-79 are depicted on FIG. 5B. The method 40 employs a combined liquid handling and spectrophotometric apparatus in accordance with the present teachings, such as the apparatus 1 depicted in FIG. 1, to determine a total concentration of a class of compounds within a sample and then employs the same apparatus to dispense a quantity of the sample for further handling, processing or analysis, wherein the dispensed quantity is based on the determined concentration. In a particular example, the dispensed quantity is employed for solid phase extraction or chromatographic or mass spectrometric analysis and is thus dispensed to an inlet port of either a separation column, a chromatograph or a mass spectrometer in the final step (step 79) of the method. However, the practice of the method 40 is not limited to that particular example.

In step 41 of the method 40, the needle capillary, the optical/flow cell, associated tubing segments and possibly the syringe pump chamber may be washed. If the fluidic system is configured as depicted in FIG. 1B, then the washing step may comprise operating the syringe pump 30 so as to aspirate a wash solution into the needle capillary 8 and associated fluidic components from a source of wash solution and then dispense the wash solution to waste. Such aspiration and dispensing to waste may be repeated one or more times. Alternatively, if the fluidic system is configured as depicted in FIG. 1C, then the washing step may comprise operating the pump 38 so as to directly draw wash solution from a wash solution source 5 and cause the wash solution to flow through tubing 13b and valve(s) 21 and to continue its flow, in order, through tubing 16, chamber 27, tubing 12 and needle capillary 8. During such operation, the needle capillary 8 is preferably positioned by the robotic assembly 2 so as to dispense the wash solution to a waste container.

After the washing step, a blank signal may be measured in step 43. A "blank" signal, as the term is used herein, is a measurement that is made by the photodetector 26 with the light source 24 and the photodetector 26 functioning in their normal operating modes but in the absence of a sample in chamber 27 of the optical/flow cell. Preferably, an essentially colorless liquid having a refractive index similar to that of an anticipated sample is present in the optical beam path of the chamber 27 during the blank signal measurement. For example, the liquid present in the cell during such a blank signal measurement may be water, alcohol or a mixture of water and alcohol. In some instances, the liquid may comprise a same or similar composition as a solvent that is used to dissolve sample compounds. Since the blank signal measurement relates to overall system operation, the step 43 is not generally required prior to each and every sample measurement. Alternatively, a blank signal or additional blank signal measurement may be obtained when the chamber contains only air. This latter measurement may be useful in determining, during execution of the following step 43, when a liquid has replaced air within the illuminated volume of the chamber 27.

After completion of step 41 and, optionally, step 43, execution of the method 40 proceeds to step 45, at which the needle capillary is moved downward into a sample-containing vial until it makes contact with bottom of the vial. The contact between the needle and vial may be detected by a force sensor coupled to servo motors of the robotic assembly 2 that drive the robotic arm 4 vertically up and down. After contact with the vial bottom has been noted, the needle capillary is then drawn slightly upward (step 47) so that sample liquid may be aspirated. For example, the needle capillary may be raised from the bottom by a distance of approximately 0.5 mm. Once the needle capillary is in position, execution proceeds to step 49 at which a portion of a sample (or all of the sample, in the case of very-small-volume samples) is aspirated into the needle capillary and the optical/flow cell until the entirety of the optical beam cross section is occluded by the sample or sample portion in the cell. In operation, this step may be effected by causing a piston of a syringe pump that is fluidically coupled to the cell and needle capillary to move in a direction that partially withdraws the piston from an enclosing cylindrical chamber. If the piston movement is actuated by a stepper motor, then the aspiration step 49 may make use of a prior counting of the number of steps of the stepper motor that are required to ingest the upper meniscus of an aspirated fluid to a position above the top of the optical illuminated volume within the chamber 27 of the optical/flow cell. Alternatively, the optical signal detected by continuously monitoring the signal of the photodetector 26 during the aspiration. The continuous monitoring may be used to detect the interruption of the optical signal at the time that the upper meniscus passes through the illuminated volume. Subsequent return to a constant (but different) optical signal during further aspiration provides an indication of single-phase liquid flow through the illuminated volume.

Once it is determined that the sample or sample portion is in the correct position, an optical transmittance measurement of the sample or sample portion is made (step 51) at one or more pre-determined wavelengths. Preferably, operation of the pump is halted during the optical measurement. The one or more wavelengths will include at least one wavelength that is at or within a known absorption feature of an analyte of interest and may also include one or more wavelengths at which reference signal measurements are made. A "reference" signal, as used in this context, is a transmittance signal that is measured at a wavelength that is displaced from the wavelength of an expected absorption feature while a sample is present within the illuminated volume. Such reference signals provide information regarding non-analyte-related background absorption and can assist in correcting analyte-specific signal from for the presence of background "noise". From a knowledge of the optical path length through the sample, which is essentially a distance between two windows between which the sample or sample portion is disposed, the corrected optical transmittance measurements may be converted to optical absorbance determinations. These may then be used to calculate a concentration (or concentrations) of one or more analytes in the sample in step 53.

According to one specific example, the analytes of interest are proteins and/or polypeptides and the analyte-specific signal is measured at the wavelength 280 nm which corresponds to the strong absorption associated with aromatic rings in the amino acid tryptophan. In such instances it is convenient to obtain a reference signal at 340 nm, which is away from any known protein or polypeptide absorption features. The optical measurement provides a measure of the concentration of tryptophan in the sample, in terms of moles per microliter. Since the relative proportions of various amino acids in biological samples are roughly constant, the tryptophan concentration measurement enables an estimation of the total concentration of amino acids, in terms of moles per microliter. This estimate can then be used to make an estimate of the average chain length of all polypeptides and proteins in the sample. Finally, the latter information may be used to make an estimate of the number of moles of all polypeptide and protein molecules per microliter of sample.

Steps 55 through 79 of the method 40 are additional operational steps that rely on the concentration determination made in step 53. Step 55 is a branching step that routes execution of the method according to whether or not the analyte(s) in the sample are determined to be present in too great a concentration. If analytes in a small sample are overly concentrated, then further handling or analysis steps may needlessly waste sample. Thus, if the sample is determined to overly concentrated in analytes, then steps 57-63 are executed. In step 57, the sample is returned to a container, such as its original container. Preferably, the container is a vial that comprises a conical narrowing of its internal volume in a downward direction. In optional step 59, the needle capillary and/or optical cell may be washed in order to prevent contamination of a diluent liquid in subsequent steps. In step 61, an appropriate quantity of the diluent liquid is aspirated into the needle capillary and possibly one or more of the optical cell, the tubings in fluidic communication with the needle and cell and a syringe pump, depending on the quantity of diluent required to bring the analytes to in the sample to a desired concentration. Then, in step 63, the diluent is dispensed into the sample container.

Step 69 of the method 40 (FIG. 5B) is executed after execution of either step 55 or step 63. In this step, a calculation is made of a quantity (in microliters) of the sample (or of the diluted sample) that corresponds to a molar amount of analyte that is desired to be dispensed for further handling, processing or analysis steps. If the sample or sample portion was not previously diluted (i.e., in steps 55-63), then the sample is already contained within the needle capillary and/or flow cell and associated tubing. In such cases, the branching step 71 may immediately direct execution to step 79, at which the calculated quantity of sample is dispensed. However, in the event that, upon reaching step 71, the sample has been previously diluted (i.e., in steps 55-63), then the sample has been returned to a container during the prior dilution process. In such cases, steps 73, 75 and 77 are executed in order to make the required quantity of sample available in the dispensing apparatus (e.g., needle capillary 8 and possibly other components fluidically coupled to the needle capillary such as tubing 12, the chamber 27 of the optical/flow cell, tubing 16 and the chamber of pump 30).

Execution of the method 40 arrives at step 79 from either step 71 or step 77. If the dispensed quantity is subjected to solid phase extraction or chromatographic or mass spectrometric analysis, then the calculated quantity is dispensed, in step 79, to an inlet port of either a separation column, a solid phase extraction column, a separation column, a chromatograph or a mass spectrometer. If the calculated quantity of the sample is greater than the quantity that is already in the dispensing apparatus but if additional sample is available in the original container, then it may be necessary to aspirate additional sample to make up the difference. If the calculated quantity of the sample is greater than the total quantity of sample that is available, then it may be necessary to either to dispense the entire available sample or to augment the sample through additional sample collection. If the calculated quantity of the sample is less than the total quantity of available sample, then any remaining sample may be returned to its original container after execution of step 79.

Figure 6:
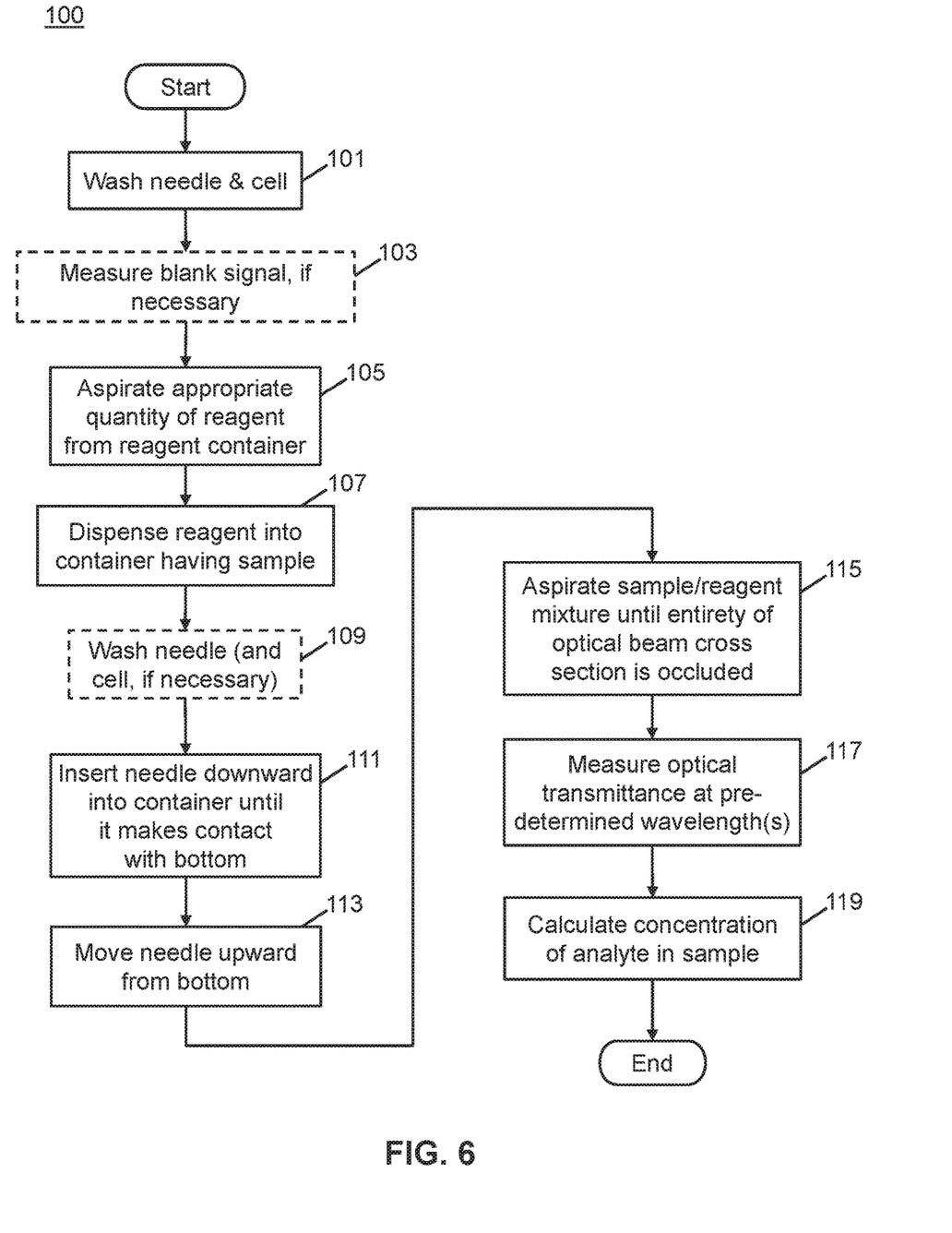
FIG. 6 is a flow diagram of a method, in accordance with the present teachings, of using a combined liquid handling and spectrophotometric apparatus to perform a colorimetric assay of a sample.

FIG. 6 is a flow diagram of an operational method 100, in accordance with the present teachings, of using a combined liquid handling and spectrophotometric apparatus to perform a colorimetric assay of a sample. In the initial step 101, of the method 100, the needle capillary, the optical/flow cell, associated tubing segments and possibly the syringe pump chamber may be washed as previously described. In step 103, a "blank" signal is measured, if required. In step 105, a quantity of a reagent is aspirated into the dispensing apparatus (e.g., needle capillary 8 and possibly other components fluidically coupled to the needle capillary as noted above) from a reagent container. In general, the reagent is a chemical compound that selectively reacts with one or more analytes in a sample and, in so reacting, generates a product compound that has a distinctive optical absorption feature or absorption spectrum. The added quantity of reagent is generally in excess of a quantity of reagent that is anticipated to drive the reaction(s) to completion. Subsequent measurement of the magnitude of the resultant optical absorption, when taken in combination with the known optical path length of the optical/flow cell, thereby provides a measure of the concentration of the one or more analytes originally present. After the reagent has been dispensed, the dispensing apparatus may be washed (step 109).

Steps 111 and 113 of the method 100 are identical to previously-described steps 45 and 47 of the method 40. After execution of these steps, the sample/reagent mixture is aspirated (step 115) until the entirety of optical beam cross section is occluded. This step may be performed in accordance with the general discussion of step 49 of the method 40. Next, in step 117, the optical transmittance is measured at one or more wavelengths that are known to correspond to optical absorption features of the anticipated product compound. This measurement enables calculation of the concentration of the product compound which, in turn, enables calculation of the original concentration of the analyte compound(s) in step 119.

In another method in accordance with the present teachings, an apparatus as described herein may be employed to provide a measurement of the total volume (in micro-liters) of a sample that is only available in a quantity that is less than a milliliter or even less than 10 μL. The method takes advantage of the facts that: (1) a cross sectional area of the internal chamber 27 of the optical/flow cell is accurately known; (2) a precision syringe pump may be operated so as to cause fluid flow rates as slow as 0.03 µL per second; and (3) an upper and a lower meniscus of the sample, moving as a plug of fluid through the chamber, may be detected optically. According to the method, the signal from the optical detector is monitored in real time as the plug of liquid is slowly and continuously aspirated up towards, into and completely through the illuminated volume of the chamber 27 at a controlled flow rate. Prior to the plug of fluid reaching the illuminated volume, the observed signal corresponds to light from the light source passing through air between the bounding windows 34a, 34b. This signal is briefly interrupted by light refraction and reflection as the top meniscus passes through the illuminated volume. The time of such interruption may be noted. The signal then remains constant as the main volume of the plug of liquid passes through the illuminated volume. A second interruption of the optical signal then indicates passage of the lower meniscus through the illuminated volume. The time of this second interruption may also be noted. The volume of liquid in the plug may be calculated from these measurements. Preferably, the calculation should make allowance for the wetting angle at each meniscus. The sample may then be fully dispensed back into its container. A replicate measurement of the volume may be made during the dispensing.

Improved methods and apparatuses for combined handling and spectrophotometry of small liquid samples have been herein disclosed. The discussion included in this application is intended to serve as a basic description. The present invention is not intended to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims. Any patents, patent applications, patent application publications or other literature mentioned herein are hereby incorporated by reference herein in their respective entirety as if fully set forth herein, except that, in the event of any conflict between the incorporated reference and the present specification, the language of the present specification will control.

What is claimed is:

1. A spectrophotometric and liquid handling system comprising:
   a robotic arm;
   a needle capillary rigidly coupled to the robotic arm;
   an optical/flow cell comprising:
      a housing;
      a first and a second window disposed within the housing and defining a width of an internal chamber therebetween;
      a collimating lens optically coupled to the first window;
      a focusing lens optically coupled to the second window;
      a fluidic inlet port fluidically coupled to a first end of the internal chamber; and
      a fluidic outlet port fluidically coupled to a second end of the internal chamber;
   a fluidic pump;
   a first and a second tubing fluidically coupled, respectively, between the needle capillary and the fluidic inlet port and between the fluidic pump and the fluidic outlet port;
   a light source;
   a photodetector; and
   a first and a second optical fiber optically coupled, respectively, between the light source and the collimating lens and between the photodetector and the focusing lens,
   wherein the optical/flow cell, the light source and the photodetector are mounted onto the robotic arm or a mounting structure thereof and are configured to move together with movement of the robotic arm.

2. A system as recited in claim 1, wherein the internal chamber comprises a volume of less than or equal to 200 micro-liters (µL).

3. A system as recited in claim 2, wherein the internal chamber comprises a volume of less than or equal to 100 micro-liters (µL).

4. A system as recited in claim 1, wherein the fluidic outlet port is disposed substantially vertically above the fluidic inlet port and the needle capillary is disposed below the fluidic inlet port.

5. A system as recited in claim 1, wherein the width of the internal chamber is in the range 1.0 to 1.5 millimeters (mm).

6. A system as recited in claim 1, wherein the light source, first optical fiber, collimating lens and first window are configured such that, in operation, a collimated light beam is provided between the first and second windows that has a total volume in the range of 3-5 $mm^3$ between the two windows.

7. A system as recited in claim 1, further comprising:
   a multiport valve fluidically coupled to both the fluidic pump and the second tubing;
   a second fluidic pump fluidically coupled to the multiport valve; and
   a source of a washing solution fluidically coupled to the second pump.

8. A system as recited in claim 1, further comprising:
   a set of fasteners that fasten the first and second windows to the housing;
   a respective set of o-rings disposed between each fastener and the housing; and
   a first and a second gasket disposed, respectively, between the first window and the housing and the second window and the housing,
   wherein the fasteners, gaskets and o-rings are configured such that the chamber is leak-tight up to pressures of 10 bars within the internal chamber.

9. A system as recited in claim 1, wherein the capillary needle is configured to mate, in a leak-tight fashion, with an inlet port receptacle of a solid phase extraction (SPE) cartridge, an injector port of a chromatograph or an inlet port of a mass spectrometer.

* * * * *